United States Patent
Darby, II et al.

(10) Patent No.: US 11,000,399 B2
(45) Date of Patent: May 11, 2021

(54) MEDICAL SHOE HAVING A DUAL-HARDNESS OUTSOLE

(71) Applicant: DARCO INTERNATIONAL, INC., Huntington, WV (US)

(72) Inventors: H. Darrel Darby, II, Mount Pleasant, SC (US); Wu Zhang, Proctorville, OH (US)

(73) Assignee: DARCO INTERNATIONAL, INC., Huntington, WV (US)

( * ) Notice: Subject to any disclaimer, the term of this patent is extended or adjusted under 35 U.S.C. 154(b) by 0 days.

(21) Appl. No.: 15/730,974

(22) Filed: Oct. 12, 2017

(65) Prior Publication Data

US 2019/0110918 A1  Apr. 18, 2019

(51) Int. Cl.
| | |
|---|---|
| A61F 5/01 | (2006.01) |
| A43B 3/12 | (2006.01) |
| A43B 13/14 | (2006.01) |
| A43B 23/08 | (2006.01) |

(52) U.S. Cl.
CPC ............ *A61F 5/0195* (2013.01); *A43B 3/128* (2013.01); *A43B 13/145* (2013.01); *A43B 23/08* (2013.01)

(58) Field of Classification Search
CPC ....... A61F 13/043; A61F 5/0195; A43B 3/128
See application file for complete search history.

(56) References Cited

U.S. PATENT DOCUMENTS

| | | | | |
|---|---|---|---|---|
| 2,278,626 A | * | 4/1942 | Vasko | A61F 13/043 36/81 |
| 3,198,192 A | * | 8/1965 | O'Brien | A61F 5/0195 602/10 |
| 4,351,324 A | * | 9/1982 | Bronkhorst | A61F 5/0195 602/27 |
| 4,546,557 A | * | 10/1985 | Barouk | A61F 5/0195 36/11.5 |
| 4,677,767 A | | 7/1987 | Darby | |
| 4,726,127 A | * | 2/1988 | Barouk | A61F 5/0195 36/110 |
| 4,774,775 A | * | 10/1988 | Pruitt | A43B 5/0419 36/117.4 |
| 5,088,481 A | * | 2/1992 | Darby | A61F 13/043 36/102 |

(Continued)

FOREIGN PATENT DOCUMENTS

WO    2009/069926 A1    6/2009

OTHER PUBLICATIONS

International Search Report dated Dec. 12, 2018 in PCT/US2018/051459.
Written Opinion dated Dec. 12, 2018 in PCT/US2018/051459.

*Primary Examiner* — Jila M Mohandesi

(74) *Attorney, Agent, or Firm* — Sughrue Mion, PLLC

(57) ABSTRACT

A dual-hardness outsole includes a front section, a middle section, and a rear section, at least the middle section of the outsole including a wedge having a bottom surface which extends below another bottom surface of at least one of the front and rear sections such that the wedge carries more weight than the other bottom surface. The outsole comprises a hard portion and a soft portion that are secured to each other and together form the wedge, a cross-sectional profile of the hard and soft density portions being such that a center portion of the wedge is softer than opposite lateral portions thereof.

22 Claims, 8 Drawing Sheets

(56) References Cited

U.S. PATENT DOCUMENTS

| | | | | |
|---|---|---|---|---|
| 5,138,777 | A | * | 8/1992 | Darby .................. A43B 13/148 36/88 |
| 5,452,527 | A | * | 9/1995 | Gaylord, Jr. .......... A61F 5/0195 36/11.5 |
| 5,491,909 | A | | 2/1996 | Darby |
| 5,551,225 | A | * | 9/1996 | Maruki .................. D01H 1/115 57/315 |
| 5,940,992 | A | * | 8/1999 | Darby ..................... A43B 7/00 36/103 |
| 7,231,728 | B2 | * | 6/2007 | Darby .................... A43B 3/128 36/100 |
| 7,500,324 | B1 | * | 3/2009 | Power .................. A43B 13/145 36/132 |
| 8,402,678 | B1 | * | 3/2013 | Kopelman ............ A61F 5/0195 36/103 |
| 8,601,722 | B2 | * | 12/2013 | Frye ....................... A43B 3/163 36/140 |
| 2009/0307925 | A1 | * | 12/2009 | Pfister .................... A43B 7/223 36/28 |
| 2012/0073166 | A1 | * | 3/2012 | Bryla .................. A43B 1/0081 36/132 |
| 2017/0273400 | A1 | * | 9/2017 | Penka ..................... A43B 5/00 |

* cited by examiner

MEDICAL SHOE HAVING A DUAL-HARDNESS OUTSOLE

BACKGROUND

This disclosure relates generally to a medical shoe to aid in the offloading or reducing the weight bearing pressure on an area of a foot, and more particularly, a medical shoe with a dual-hardness outsole for increasing the shoe's stability during movement and promoting faster healing of a foot condition or ailment.

To promote healing of a foot condition or ailment, a patient may be fitted with footwear that reduces the weight bearing pressure on a specific area of the foot. This foot condition or ailment may arise following surgery, trauma, or when ulcerations or wounds are present. Typically, the provided footwear may have an overly rigid sole, either in the front or rear of the shoe, requiring the patient to walk in a certain manner to properly use the shoe. For instance, a medical shoe configured to remove the weight bearing pressure on the forefoot may have a sole in which the rear area of the sole, extending from the heel to midfoot, is larger than the front area of the sole, extending to the midfoot to forefoot. In other words, the rear area of the sole is disposed in a manner so that the front area of the sole is elevated from the ground level when the medical shoe is in a midstance phase of the patient's gait. See U.S. Pat. Nos. 5,491,909 and 7,231,728, which are incorporated herein by reference.

Due to the unusual shape of the overly rigid sole from that of a typical street shoe or sneaker, the healthcare provider may require the patient to walk in a certain manner so as to take full benefit of the medical shoe and not further delay the healing of the condition or ailment in the forefoot area. For example, in order to avoid weight on the forefoot, the health care provider may instruct the patient to shift his or her weight to the heel by having the patient first make contact with the heel (i.e., the heel strike which is the initial contact phase during normal gait) then to the midfoot (i.e., the midstance phase during which the opposite raised leg passes the ground leg), followed by lifting the foot without pushing off with the toes (i.e., toe-off phase which is the final gait phase in which the forefoot propels the body forward). However, most patients do not walk as instructed and push off with their toes, creating pressure on the forefoot and delaying the healing process or further injuring the forefoot.

SUMMARY

In an exemplary embodiment, a dual-hardness outsole including a front section, a middle section, and a rear section, at least the middle section of the outsole including a wedge having a bottom surface which extends below another bottom surface of at least one of the front and rear sections such that the wedge carries more weight than the other bottom surface, the outsole comprising: a hard portion and a soft portion that are secured to each other and together form the wedge, a cross-sectional profile of the hard and soft density portions being such that a center portion of the wedge is softer than opposite lateral portions thereof.

In another exemplary embodiment, A medical shoe including an upper assembly configured to secure a foot to the medical shoe, an insole configured to support a plantar portion of the foot, and a dual-hardness outsole including a front section, a middle section, and a rear section, at least the middle section of the outsole including a wedge having a bottom surface which extends below another bottom surface of at least one of the front and rear sections such that the wedge carries more weight than the other bottom surface, the outsole comprising: a hard portion and a soft portion that are secured to each other and together form the wedge, a cross-sectional profile of the hard and soft density portions being such that a center portion of the wedge is softer than opposite lateral portions thereof.

BRIEF DESCRIPTION OF DRAWINGS

FIG. 1 is a perspective view of a medical shoe having a dual-hardness outsole for offloading or reducing the weight bearing pressure on a forefoot.

FIG. 2 is a perspective view of a second portion of a dual-hardness outsole.

FIG. 3 is a perspective view of a dual-hardness outsole for offloading or reducing the weight bearing pressure on a forefoot area of a foot.

FIG. 4 is a longitudinal cross-section view at the center of the medical shoe.

FIG. 5 is a horizontal cross-section view at a middle area of the medical shoe.

FIG. 6 is a perspective view of a medical shoe having a dual-hardness outsole for offloading or reducing the weight bearing pressure on the hindfoot or a rear area of a foot.

FIG. 7 is a longitudinal cross-section view at the center of the medical shoe.

FIG. 8 is a horizontal cross-section view at a middle area of the medical shoe.

DETAILED DESCRIPTION

Figure 1:
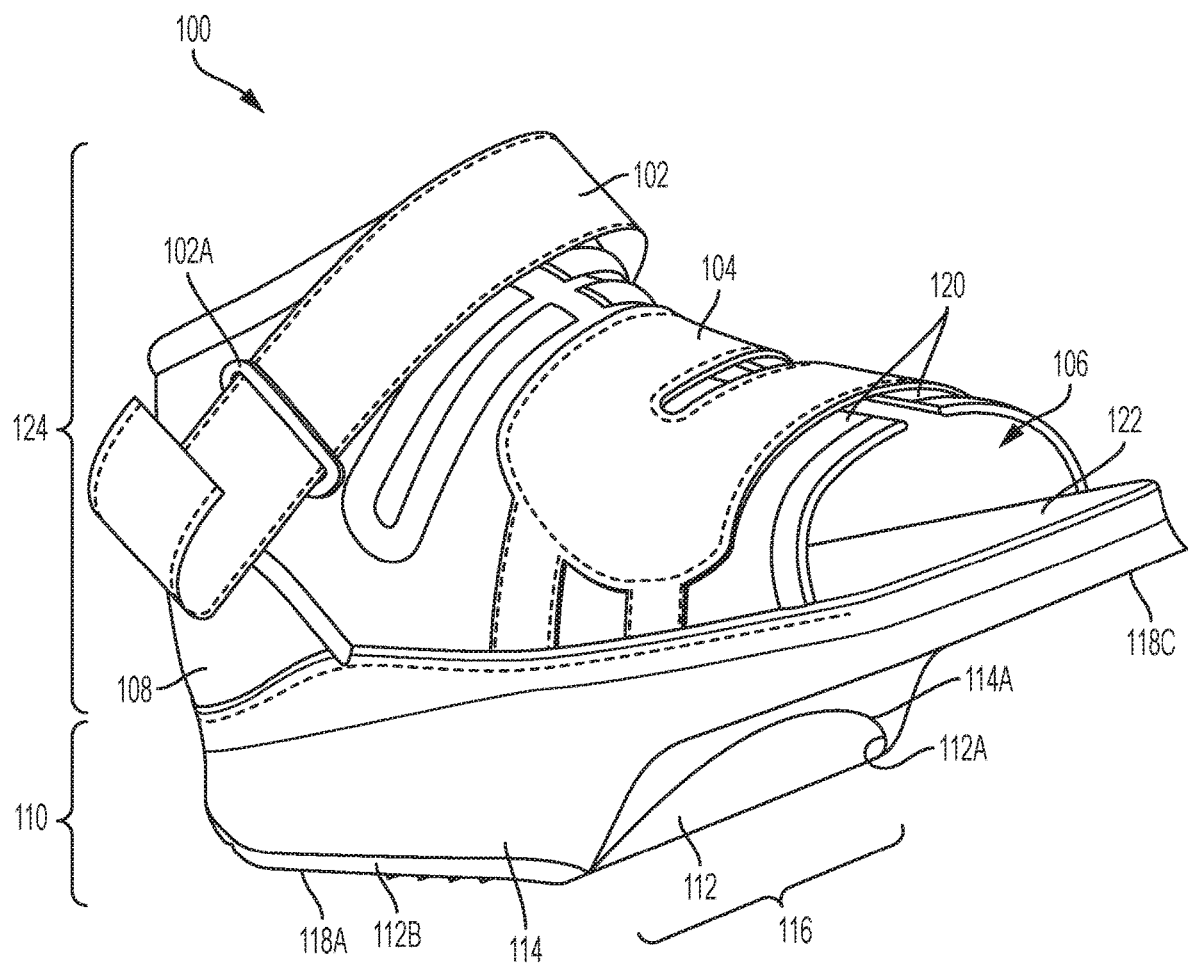
FIGS. 1 through 5 describe a first exemplary embodiment of a medical shoe having a dual-hardness outsole for offloading or reducing the weight bearing pressure on a forefoot.

This description of the exemplary embodiments is intended to be read in connection with the accompanying drawings, which are to be considered part of the entire written description. In the description, relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Exemplary embodiments of the present disclosure relate generally to a medical shoe to aid in the offloading or reducing the weight bearing pressure on an area of a foot, and more particularly, to a medical shoe with a dual-hardness outsole for increasing the shoe's stability during movement and promoting faster healing of a foot condition or ailment. Exemplary embodiments which increase stability of a medical shoe and promote healing are described below with reference to FIGS. 1-8.

A First Exemplary Embodiment

FIGS. 1-5 illustrate a medical shoe according to one embodiment of the present disclosure. FIG. 1 is a perspective view of a medical shoe 100 having a dual-hardness outsole 110 for offloading or reducing the weight bearing pressure on a forefoot. The medical shoe 100 comprises an upper assembly 124, the dual-hardness outsole 110, and an insole 122.

The upper assembly 124, comprising a heel portion 108 and sidewalls 120, is configured to surround the heel, sides, and a dorsal portion of a foot to secure the shoe to the foot such as disclosed in U.S. Pat. Nos. 5,940,992 and 4,677,767, which are incorporated herein by reference. The upper assembly 124 may comprise an inner and outer layer. The inner layer can comprise a soft fabric to cushion the foot from the sidewalls 120 and heel portion 108 when the upper assembly 124 is secured to the foot. The outer layer can comprise nylon mesh, leather, canvas, or other material suitable for flexibly surrounding the heel, sides, and a dorsal portion of the foot. The inner layer and outer layer can be integrally connected to one another.

Figure 6:
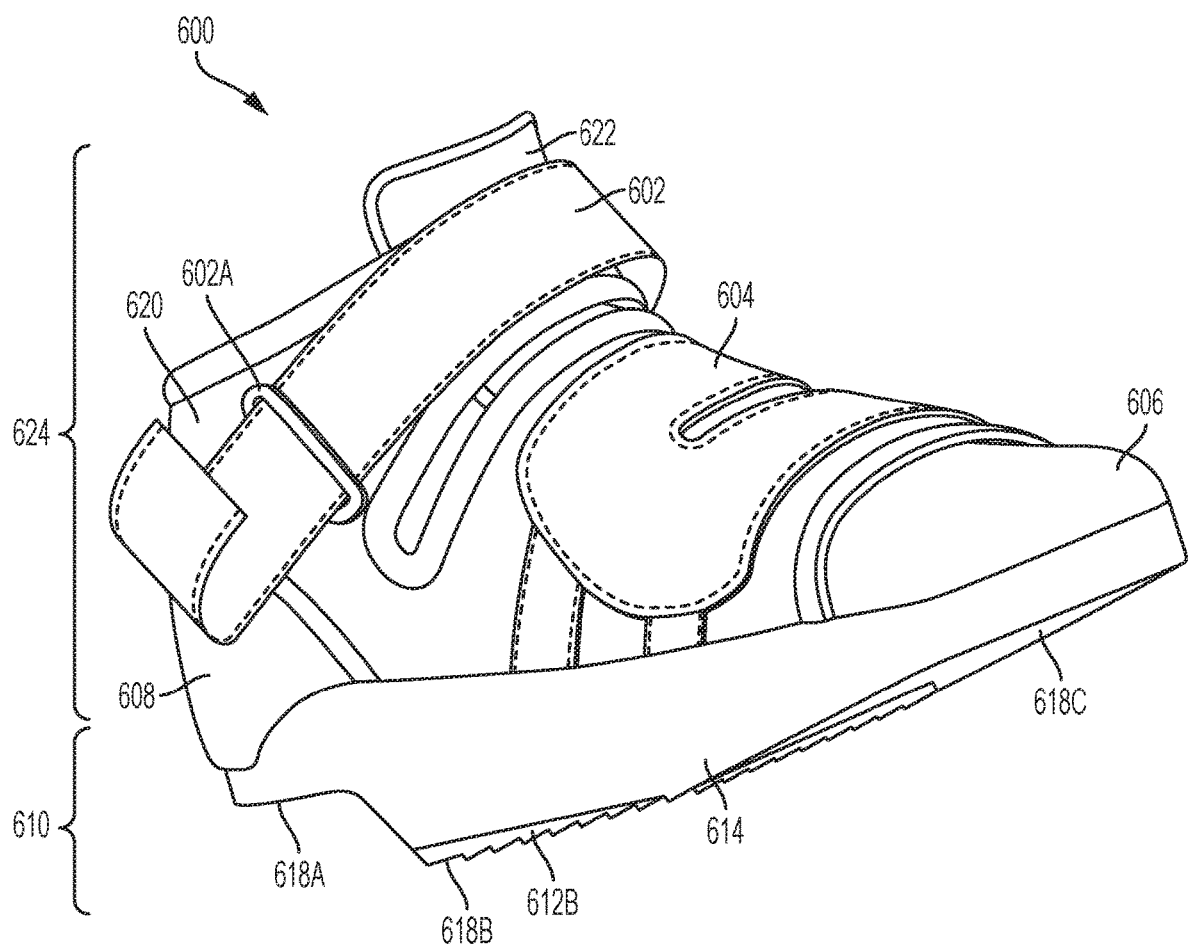
FIGS. 6 through 8 describe a second exemplary embodiment of a medical shoe having a dual-hardness outsole for offloading or reducing the weight bearing pressure on a hindfoot or a rear area of a foot.

The upper assembly 124 can be secured to a foot in a variety of ways known to one or ordinary skill in the art. For example, the sidewalls 120 can be configured to overlap one another in which the sidewalls are fastened together using Velcro® or buttons. In another example, the sidewalls 120 can be laced together. Additionally, sidewalls 120 may be configured in a similar manner to sidewall 620, as shown in FIG. 6.

The upper assembly 124 can be secured to a foot using hooks and loop straps. An upper strap 102, configured to secure the rear area of the foot to the medical shoe 100, may be secured to one sidewall and extend transversely to the opposite sidewall. The patient, medical provider, or a third party can fasten the rear area of the foot to the medical shoe 100 by threading the upper strap 102 through a hook 102A and back to a starting area of strap 102. The person fastening the upper strap 102 can fasten the beginning and end area of the strap 102, using a fastening means know by one of ordinary skill in the art such as Velcro® or buttons.

A pair of lower straps 104, configured to secure the front area of the foot to the medical shoe 100, may be attached to one sidewall and extend transversely to the opposite sidewall to be fastened, securing the front area of the foot. In an exemplary embodiment, the pair of lower straps 104 may be joined at one end and branch into a plurality of lower straps that extend transversely to the opposite sidewall to provide even tension on the dorsal portion of the foot. In another exemplary embodiment, one lower strap or more than one lower strap, being separate from each other, may each be attached to one sidewall and extend transversely to the opposite sidewall to be fastened, securing the front area of the foot.

The upper assembly 124 may comprise an open-toe area 106 to accommodate space for various items such as medical dressings, bandages, pins, etc. A toe cover (not shown) may be installed to cover the open toe area 106 to protect a patient's toes.

Figure 3:
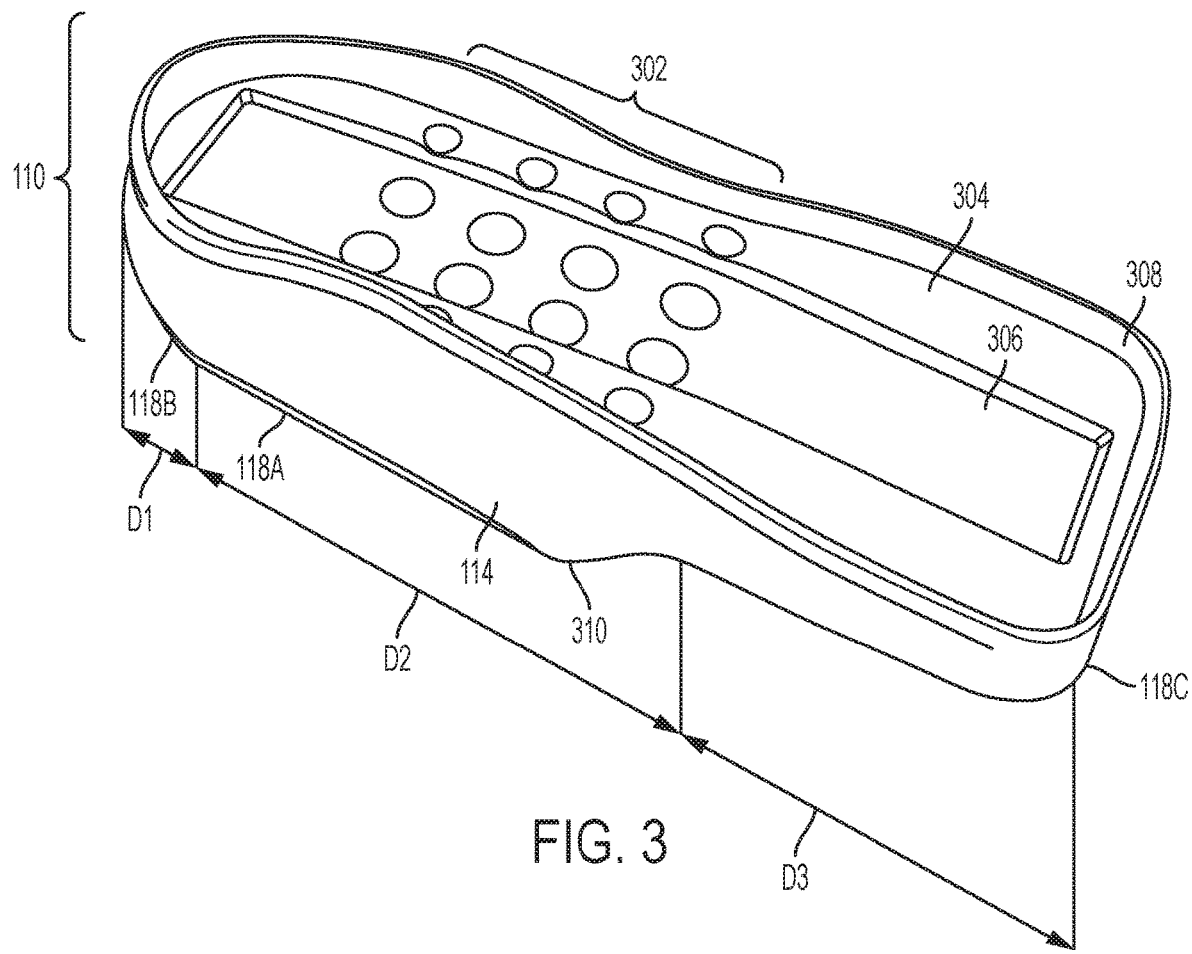

As discussed below, the dual-hardness outsole 110 is configured to provide a cushion to the heel and midsection of the foot while at the same time providing lateral stability to the foot. The dual-hardness outsole 110 is secured to the upper assembly 124 by conventional means such as by stitching, gluing, or the like. To assist in that regard, the dual-hardness outsole 110 may include an upwardly extending circumferential portion 308 (as shown in FIG. 3) that is secured to the upper assembly 124.

As discussed below, the dual-hardness outsole 110 is divided longitudinally into three different sections including rear section D1, middle section D2, and front section D3. The thickness of the front section D3 is reduced as compared to the thickness of the rear and middle sections D1 and D2 such that the weight of the patient is carried mainly by the rear section D1 and the middle section D2. That is, the bottom surface 118C of the outsole 110 is recessed upwardly at the front section D3 to remove or minimize the weight from this front section D3 of the shoe (the un-weighted section). The rear section D1 is tapered.

The dual-hardness outsole 110 comprises a first relatively hard portion 114 and a second relatively soft portion 112. The hard portion 114 and soft portion 112 are secured to one another to form a wedge 116. The hard portion 114 has a greater hardness than the soft portion 112. For example, the hard portion 114 may have a hardness of shore C 60 degrees and the soft portion 112 may have a hardness of shore C 45 degrees. The hard portion 114 has a recessed bottom surface 114A generally located in the middle and rear sections D2 and D1 and a forward most bottom surface 118C. The soft portion 112 is disposed in the recessed bottom surface 114A and secured thereto such that the upper surface 112A of the soft portion 112 is secured to the recess bottom surface 114A.

Figure 2:
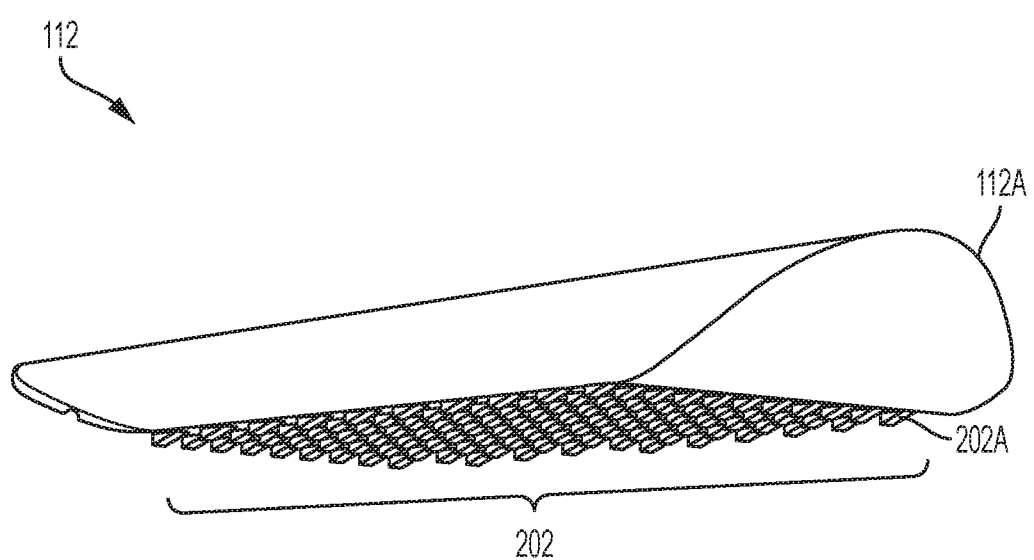

As can be seen, the soft portion 112 is shaped such that its lateral center portion is greater in thickness than its lateral outer portions. In this way, the patient's foot can experience a cushioned feel in the center of the foot while maintaining lateral stability due to the relatively shallow thickness of the lateral portions. That is, the vertical thickness of the lateral outer portions of the outsole 110 is defined by a greater mass of the hard portion 114 as compared to the mass of the soft portion 112. In contrast, in the middle portion the mass of the soft portion 112 is increased as compared to the mass of the hard portion 114. As best shown in FIGS. 1 and 2, the upper surface 112A has a curved shape such that the thickness of the soft portion 112 in the vertical direction changes gradually. However, it should be understood that the cross-sectional shape of the soft portion 112 may be different to include, for example, an upper surface having steps to achieve the gradual reduction in thickness.

The hard portion 114 and the soft portion 112 may be secured together during an injection molding process, such as ethylene-vinyl acetate (EVA) injection molding. The hard portion 114 and soft portion 112 may be made out of EVA, polyurethane (PU), thermal plastic rubber (TPR), or any other material known to one of ordinary skill in the art so long as the hard portion 114 has a greater hardness than the soft portion 112. The soft portion 112 comprises a compressible material configured to absorb the weight bearing pressure of the heal section of the foot when the heel contacts the ground and the midfoot section of a foot when the midfoot contacts the ground.

Figure 4:
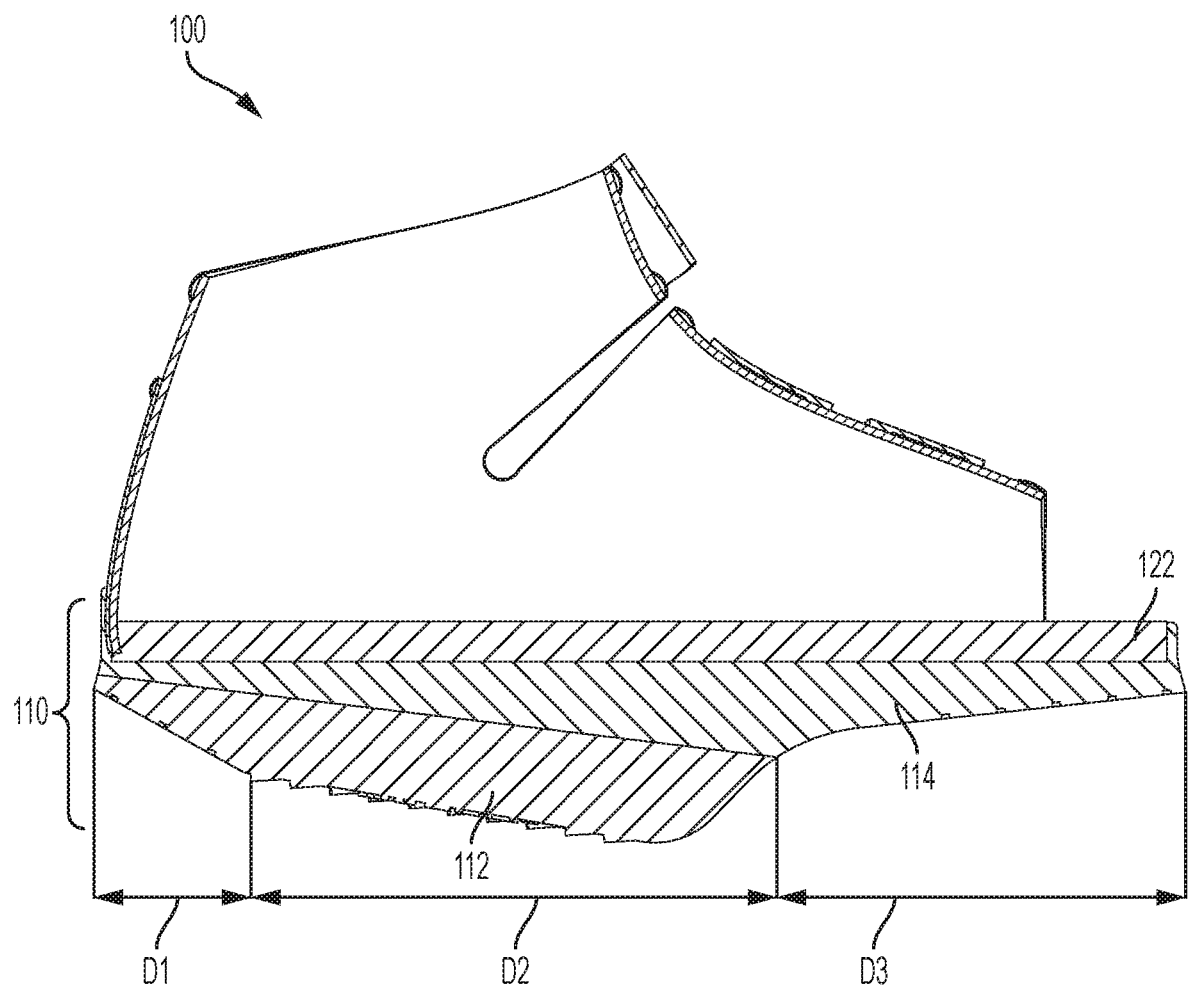

The recessed bottom surface 114A may be tapered from the middle section D2 to the rear section D1 in a longitudinal direction of the outsole 110, as shown in FIGS. 1 and 4. In some exemplary embodiments, the recessed bottom surface 114A may completely surround the upper surface 112A of the soft portion 112. In other exemplary embodiments, the recessed bottom surface 114A substantially surrounds the upper surface 112A so that only a small area 112B of the soft portion 112 is exposed on at least one of a right, left, and rear side of the medical shoe 100. The exposed small area 112B provides increased cushioning during the user's movement.

FIG. 2 is a perspective view of the second relatively soft portion 112 of the dual-hardness outsole 110. As noted above, the soft portion 112 has a curved upper surface 112A and a generally planar bottom surface 202. The bottom surface 202 has a plurality of grippers 202A thereon that provide traction to prevent the medical shoe 100 from slipping on a ground surface while a patient is moving. Each gripper 202A may be tapered towards the front section D3 of the outsole 110. That is, the plurality of grippers 202A are tapered in a direction of forward movement to smoothly contact the ground surface while providing traction. The plurality of grippers 202A may be formed using a conventional molding process.

The plurality of grippers 202A may be arranged in a variety of patterns. For example, one pattern may include, but is not limited to, a plurality of grippers extending horizontally and vertically forming multiple rows and columns. Another pattern may include a single gripper extending horizontally from one side of the medical shoe 100 to the other side, in which a plurality of these horizontal grippers are arranged to form a plurality of rows extending in a longitudinal direction of the medical shoe 100 (not shown). Another pattern may include a single gripper extending vertically across the soft portion 112, in which a plurality of these vertical grippers are arranged to form a plurality of columns extending in a lateral direction of the medical shoe 100 (not shown). It should be appreciated that the above mentioned arrangement of plurality of grippers 202A is not an exhaustive list, and that arrangements of the plurality of grippers 202A may be formed as appreciated by one of ordinary skill in the art.

As discussed above, the upper surface 112A of the soft portion 112 may be curved in a lateral direction of the dual-hardness outsole 110. Also, the soft portion 112 is tapered in a longitudinal direction towards a rear section D1 of the dual-hardness outsole 110. The peak of the curved upper surface 112A is positioned in an area of the medical shoe 100 providing a maximum crumple zone to absorb the weight bearing pressure of at least one of the midfoot and heel section of the foot. The peak of the curved upper surface 112A may align with the center of the medical shoe 100 in a longitudinal direction.

Figure 5:
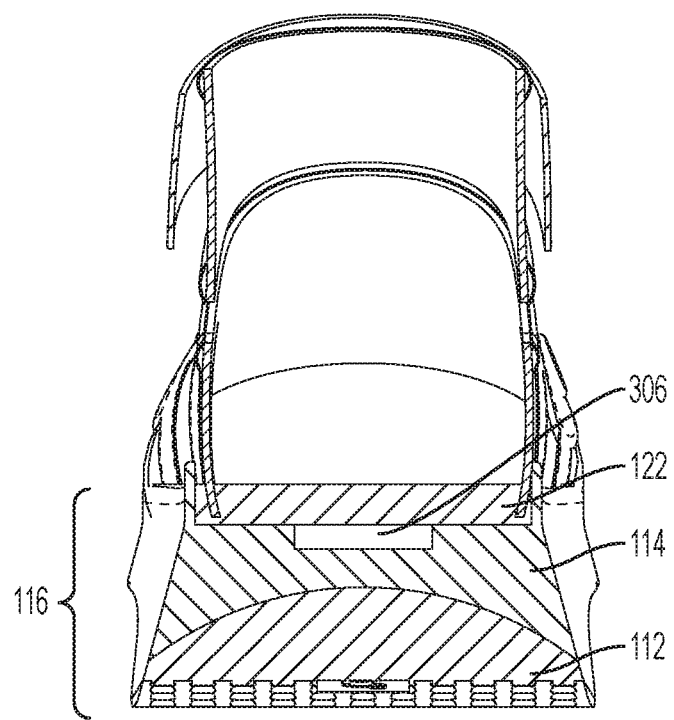

FIG. 3 is a perspective view of a dual-hardness outsole 110 for offloading or reducing the weight bearing pressure on a forefoot area of a foot. FIG. 4 is a longitudinal cross-section view at the center of the medical shoe 100. FIG. 5 is a horizontal cross-section view at a middle section D2 of the medical shoe 100.

As noted above, the dual-hardness outsole 110 comprises a rear section D1, a middle section D2, and a front section D3. The dual-hardness outsole 110 can be tapered towards a rear of the shoe, as shown in FIG. 1. The front section D3 extends in a longitudinal direction from a frontal end of the dual-hardness outsole 110 to a frontal end of the middle section D2. At the frontal end of the middle section D2, the bottom surface of the dual-hardness outsole 110 slopes downward to a frontal point of contact 310 being level with a ground surface during a midstance phase. The transition of the bottom surface of the dual-hardness outsole 110 from a frontal end of the middle section D2 to the frontal point of contact 310 can be formed at a variety of angles and curvatures. The bottom surface 118A of the dual-hardness outsole 110 may extend from the frontal point of contact 310 to the distal end of the dual-hardness outsole 110. The bottom surface 118A located in the rear section D1 of the dual-hardness outsole 110 is formed at an oblique angle, as shown in FIG. 3. The oblique angled bottom surface 118B is configured to allow an easier ambulatory movement as a patient moves in the medical shoe 100.

Referring to FIG. 3, the dual-hardness outsole 110 may comprise an upper recessed portion 306 on a top surface 304 thereof. The upper recessed portion 306 is centered in a horizontal direction of the dual-hardness outsole 110 and extends in a longitudinal direction of the outsole 110 from a frontal end of the outsole 110 to a rear end of the outsole 110. The upper recessed portion 306 may also extend from an area of the rear section D1 to an area substantially near the end of the front section D3. The upper recessed portion 306 may extend the length of a patient's foot, that is, from a rear end of the hindfoot to a frontal end of the forefoot.

The upper recessed portion 306 is configured to accommodate a shank (shank not shown), which is designed to add rigidity to the area of the dual-hardness outsole 110 supporting at least one of the bottom surface 118C and wedge 116. In an exemplary embodiment, the shank comprises a flexible yet rigid material adapted to support a plantar portion of a foot. For example, the shank can be, but is not limited to, bamboo, rubber, wood, or plastic. In other exemplary embodiments, the upper recessed portion 306 and shank may not be included in the dual-hardness outsole 110, as shown in FIG. 4. Further, the outer circumferential portion 308 may be configured to support an insole 122 and position the insole 122 within the dual-hardness outsole 110.

As shown in FIG. 3, a plurality of holes 302 may be formed within the hard portion 114. The plurality of holes 302 may extend from the top surface 304 to an area at or above the soft portion 112. The plurality of holes 302 may be formed during the molding process of the wedge 116.

Comparing the medical shoe 100 comprising the dual-hardness outsole 110 to a medical shoe with a rigid, single hardness, outsole as described in the Background section, the dual hardness outsole according to the invention subject the foot to less pressure when walking. For instance, during the toe-off phase, an average peak pressure for the overly rigid outsole measured at 18.4 PSI, whereas an average peak pressure for the dual-hardness outsole 110 measured at 16 PSI. During the heel strike or offloading phase, an average peak pressure for the overly rigid outsole measured at 16.6 PSI, whereas an average peak pressure for the dual-hardness outsole 110 measured at 11.25 PSI. These results show that the foot is under less overall pressure when walking using the dual-hardness outsole.

A Second Exemplary Embodiment

Figure 7:
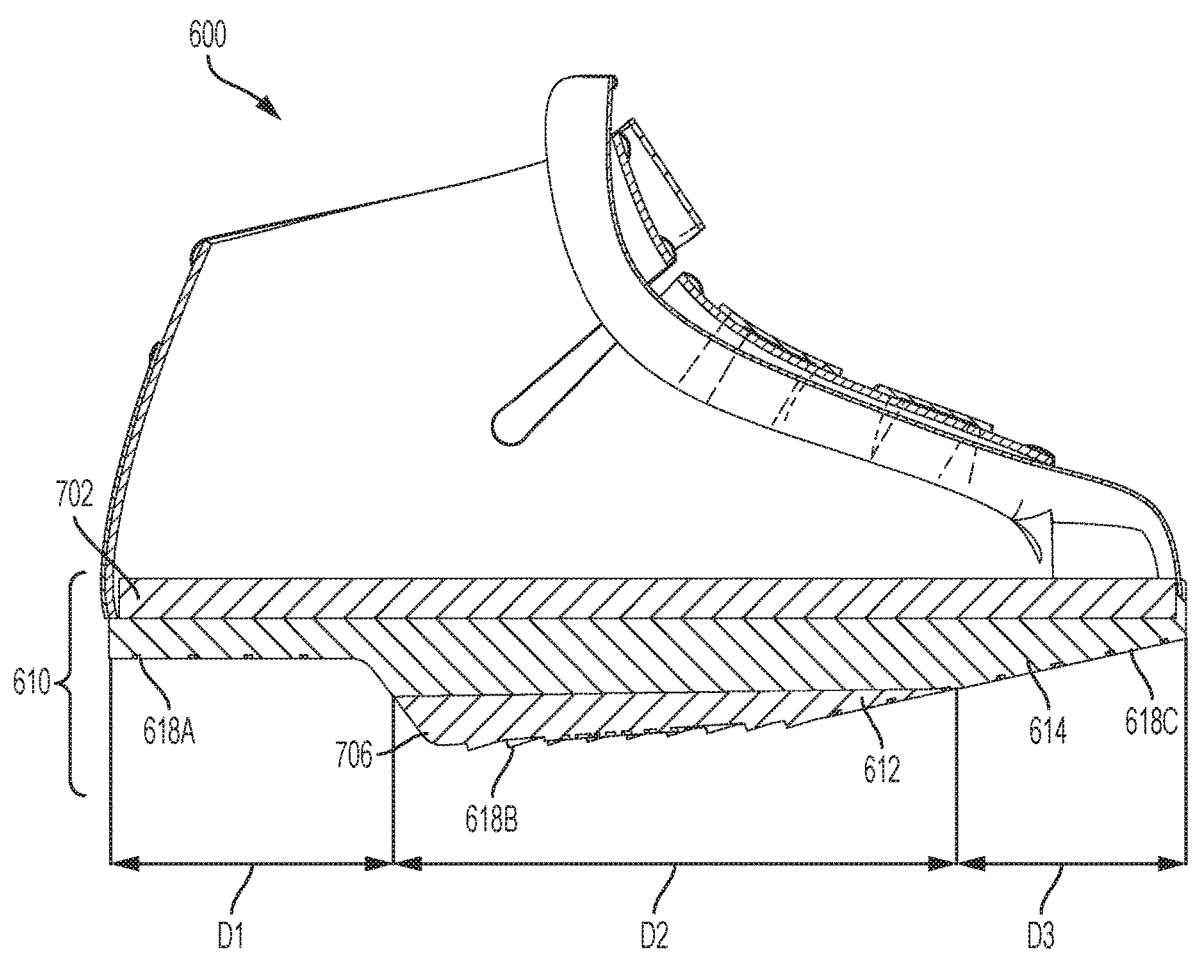
Figure 8:
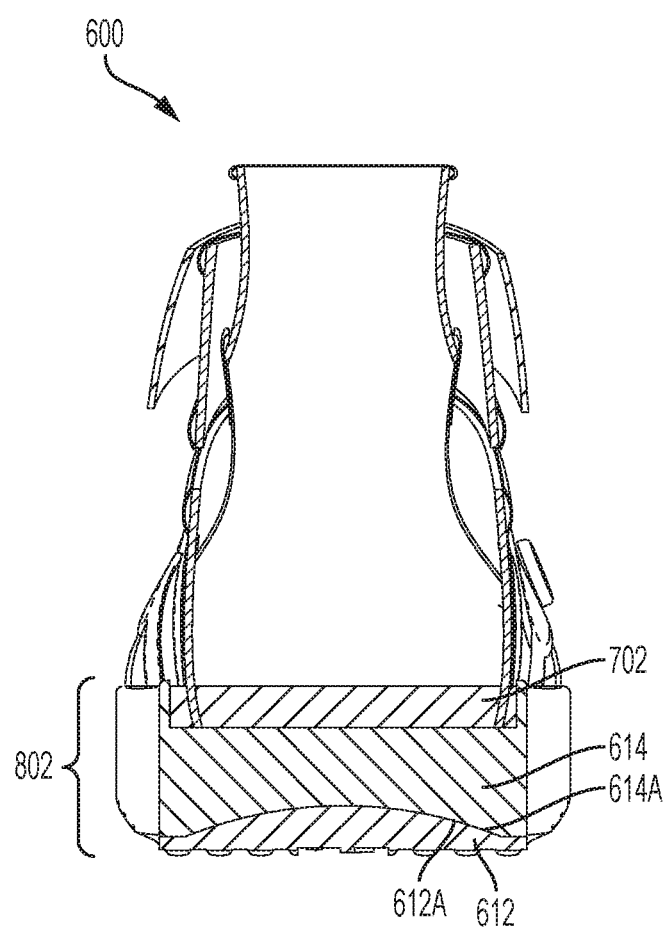

FIGS. 6-8 illustrate a medical shoe configured to offload or reduce the weight bearing pressure on the rear area or heel portion of the foot, according to another embodiment of the present disclosure. In contrast to the previous embodiment, the rear section D1 of the shoe 600 is recessed to remove or minimize the weight on this portion of the shoe. Thus, in this embodiment the rear section D1 of the shoe 600 is the un-weighted section, different from the above embodiment in which the front section D3 of the shoe 100 is un-weighted.

Upper strap 602, hook 602A, and the pair of lower straps 604 are similar to upper strap 102, hook 102A, and the pair of lower straps 104; the dual-hardness outsole 610 is secured to the upper assembly 624 in a similar manner to that of the dual-hardness outsole 110 being secured to the upper assembly 124; the soft portion 612 includes a plurality of grippers that include the features of the plurality of grippers 202; an upper recessed portion (not shown), an upwardly extending circumferential portion (not shown), and an insole 702 configured with similar features to that of the upper recessed portion 306, the outer circumferential portion 308, and insole 122. Further, a plurality of holes may be formed within the hard portion 614 in a similar manner as described above with reference to the plurality of holes 302. Thus, in view of the above, a redundant description of the aforementioned features will not be repeated. Additionally, FIGS. 7 and 8 do not illustrate the upper recessed portion configured to accommodate a shank; however, it should be understood that that dual-hardness outsole 610 can comprise the features discussed with respect to the upper recessed portion 306.

The upper assembly 624, comprising a heel portion 608 and sidewall 620, is configured to surround the heel, sides, dorsal portion, and toe area of a foot. The upper assembly 624 comprises an inner and outer layer similar to the inner and outer layer as described above with reference to upper assembly 124. Further, the upper assembly 624 is secured to the dual-hardness outsole 610 in a similar fashion as described above with reference to the dual-hardness outsole 110 and the upper assembly 124.

The upper assembly 624 is distinguishable from the upper assembly 124 in that the upper assembly 624 may include a singular sidewall 620 configured to surround a foot; a closed-toe area 606; and a tongue 622 to aid a patient in putting on the medical shoe. It should be noted that these distinguishable features may be incorporated into medical shoe 100.

The dual-hardness outsole 610 is distinguishable from the dual-hardness outsole 110 in that the dual-hardness outsole 610 is configured to provide a cushion to the midfoot and forefoot of the foot while at the same time providing lateral stability to the foot. Further, as discussed below, the dual-hardness outsole 610 is divided longitudinally into three different sections including rear section D1, middle section D2 and front section D3. The thickness of the rear section D1 is reduced as compared to the thickness of the middle and front sections D2 and D3 such that the weight of the patient is carried mainly by the middle section D2 and front section D3. That is a rearmost bottom surface 618A of the outsole 610 is recessed upwardly at the rear section D1 to remove or minimize the weight from the rear section D1 of the shoe (the un-weighted section). The front section D3 is tapered.

The dual-hardness outsole 610 comprises a first relatively hard portion 614 and a second relatively soft portion 612. The hard portion 614 and the soft portion 612 are secured to one another to form a wedges 802, as shown in FIG. 8. The hard portion 614 has a greater hardness than the soft portion 612. The hard portion 614 and soft portion 612 may be made out of the same material as the hard portion 114 and the soft portion 112, and may be secured together in a similar injection molding process as the hard portion 114 and the soft portion 112. Further, the soft portion 612 comprises a compressible material configured to absorb the weight bearing pressure of the forefoot when the forefoot contacts the ground and the midfoot section of a foot when the midfoot contacts the ground.

The hard portion 614 has a recessed bottom surface 614A generally located in the middle section D2 and a rearmost bottom surface 618A generally located in the rear section D1. The soft portion 612 is disposed in recessed bottom surface 614A and secured thereto such that the upper surface 612A of the soft portion 612 is secured to the recess bottom surface 614A. The bottom surface 614A is disposed above a bottom surface 618B of the wedge 802.

As can be seen in FIGS. 7 and 8, the soft portion 612 is shaped such that its lateral center portion is greater in thickness than its lateral outer portions. In this way, the patient's foot can experience a cushioned feel in the center of the foot while maintaining lateral stability due to the relatively shallow thickness of the lateral portions. That is, the vertical thickness of the lateral outer portions of the outsole 610 is defined by a greater mass of the hard portion 614 as compared to the mass of the soft portion 612. In contrast, in the middle portion the mass of the soft portion 612 is increased as compared to the mass of the hard portion 614. As best shown in FIG. 8, the upper surface 612A has a curved shape such that the thickness of the soft portion 612 in the vertical direction changes gradually. However, it should be understood that the cross-sectional shape of the soft portion 612 may be different to include, for example, an upper surface having steps to achieve the gradual reduction in thickness.

In some exemplary embodiments, the recessed bottom surface 614A may completely surround the upper surface 612A of the soft portion 612. In other exemplary embodiments, the recessed bottom surface 614A substantially surrounds the upper surface 612A so that only a small area 612B of the soft portion 612 is exposed on at least one of a right, left, and front side of the medical shoe 600.

As discussed above, the upper surface 612A of the soft portion 612 may be curved in a lateral direction of the dual-hardness outsole 610. Also, the soft portion 612 is tapered in a longitudinal direction towards the front section D3 of the dual-hardness outsole 610. The peak of the curved upper surface 612A is positioned in an area of the medical shoe 600 providing a maximum crumple zone to absorb the weight bearing pressure of at least one of the forefoot and midfoot of the foot. The peak of the curved upper surface 612A may align with the center of the medical shoe 600 in a longitudinal direction.

As noted above, the dual-hardness outsole 610 comprises a rear section D1, a middle section D2, and a front section D3. The dual-hardness outsole 610 is tapered towards the front of the shoe, as shown in FIGS. 6 and 7. The front section D3 extends in a longitudinal direction from a frontal end of the dual-hardness outsole 610 to a frontal end of the middle section D2. The rear section D1 extends in a longitudinal direction from a rear end of the dual-hardness outsole 610 to an end of the soft portion 612. The middle section D2 extends from a rear end of the front section D3 to the front end of the rear section D1. At the point of contact 706 to a ground surface, the bottom surface 618B of the dual-hardness outsole 610 slopes upward towards a frontal end of the bottom surface 618A. The transition of the point of contact 706 to the frontal end of the bottom surface 618A can be formed at a variety of angles and curvatures. Further, the bottom surface 618C located in the front section D3 of the dual-hardness outsole 802 is formed at an oblique angle. The oblique angled bottom surface 618C is configured to allow an easier ambulatory movement as a patient moves in the medical shoe 600.

Although the subject matter has been described in terms of exemplary embodiments, it is not limited thereto. Rather, the appended claims should be construed broadly, to include other variants and embodiments, which may be made by those skilled in the art without departing from the scope and range of equivalents of the subject matter.

What is claimed is:

1. A dual-hardness outsole including a front section, a middle section and a rear section, at least the middle section of the outsole including a wedge having a first bottom surface which extends below at least one of a second bottom surface, on the front section, and a third bottom surface, on the rear section, such that the first bottom surface carries more weight than said at least one of the second bottom surface and the third bottom surface, the outsole comprising:
a hard portion and a soft portion that are secured to each other and together form the wedge, a cross-sectional profile of the hard and soft portions in a width direction, perpendicular to a longitudinal direction that is from the front section to the middle section, of the dual-hardness outsole at the wedge being such that both a thickness of the soft portion is gradually decreased and also a thickness of the hard portion is increased as the soft portion and the hard portion are extended from a center of the wedge in the width direction towards a lateral end portion of the wedge in the width direction.

2. The dual-hardness outsole of claim 1, wherein the hard portion has a longitudinally extending recess therein and the soft portion is disposed in the recess.

3. The dual-hardness outsole of claim 2, wherein the recess has an arcuate cross-section such that a center portion of the soft portion disposed in the recess is thicker than lateral portions of the soft portion disposed in the recess.

4. The dual-hardness outsole of claim 1, wherein the hard portion extends to the front section and the rear section.

5. The dual-hardness outsole of claim 1, wherein the front section only includes the hard portion.

6. The dual-hardness outsole of claim 1, wherein the rear section only includes the hard portion.

7. The dual-hardness outsole of claim 1, wherein a top surface of the hard portion includes a longitudinally extending recess for receiving a stiffening shank.

8. The dual-hardness outsole of claim 1, wherein the hard portion and the soft portion are injected molded together.

9. The dual-hardness outsole of claim 1, wherein the wedge is tapered in a longitudinal direction of the dual hardness outsole.

10. The dual-hardness outsole of claim 9, wherein the hard portion is tapered so as to have a decreasing thickness in a front to rear direction.

11. The dual-hardness outsole of claim 1,
wherein the hard portion comprises projections configured to receive an insole therein,
wherein the soft portion comprises a flat side and a curved side,
wherein the flat side faces away from the hard portion, and
wherein the curved side faces the hard portion and is closer to the projections than the flat side is to the projections.

12. The dual-hardness outsole of claim 1,
wherein the cross-sectional profile of the hard and soft portions in the width direction, perpendicular to the longitudinal direction that is from the front section to the middle section, of the dual-hardness outsole at the wedge being further such that both the thickness of the soft portion is gradually decreased and also the thickness of the hard portion is increased as the soft portion and the hard portion are further extended from the center of the wedge in the width direction towards a second lateral end portion of the wedge in the width direction, and
wherein the second lateral end portion of the wedge is opposite to the lateral end portion of the wedge in the width direction across the wedge.

13. A medical shoe including an upper assembly configured to secure a foot to the medical shoe, an insole configured to support a plantar portion of the foot, and a dual-hardness outsole including a front section, a middle section, and a rear section, at least the middle section of the outsole including a wedge having a first bottom surface which extends below at least one of a second bottom surface, on the front section, and a third bottom surface, on the rear section, such that the first bottom surface carries more weight than said at least one of the second bottom surface and the third bottom surface, the outsole of the medical shoe comprising:
a hard portion and a soft portion that are secured to each other and together form the wedge, a cross-sectional profile of the hard and soft portions in a width direction, perpendicular to a longitudinal direction that is from the front section to the middle section, of the dual-hardness outsole at the wedge being such that both a thickness of the soft portion is gradually decreased and also a thickness of the hard portion is increased as the soft portion and the hard portion are extended from a center of the wedge in the width direction towards a lateral end portion of the wedge in the width direction.

14. The medical shoe of claim 13, wherein the hard portion has a longitudinally extending recess therein and the soft portion is disposed in the recess.

15. The medical shoe of claim 14, wherein the recess has an arcuate cross-section such that a center portion of the soft portion disposed in the recess is thicker than lateral portions of the soft portion disposed in the recess.

16. The medical shoe of claim 13, wherein the hard portion extends to the front section and the rear section.

17. The medical shoe of claim 13, wherein the front section only includes the hard portion.

18. The medical shoe of claim 13, wherein the rear section only includes the hard portion.

19. The medical shoe of claim 13, wherein a top surface of the hard portion includes a longitudinally extending recess for receiving a stiffening shank.

20. The medical shoe of claim 13, wherein the hard portion and the soft portion are injected molded or glued together.

21. The medical shoe of claim 13, wherein the wedge is tapered in a longitudinal direction of the dual hardness outsole.

22. The medical shoe of claim 21, wherein the hard portion is tapered so as to have a decreasing thickness in a front to rear direction.

* * * * *